United States Patent
Devyatov

(10) Patent No.: US 11,382,930 B2
(45) Date of Patent: Jul. 12, 2022

(54) METHOD FOR BONE TISSUE REGENERATION IN EXPERIMENTS

(71) Applicant: OOO "FELIX", Respublika Tatarstan (RU)

(72) Inventor: Fedor Vladimirovich Devyatov, Kazan (RU)

(73) Assignee: OOO "FELIX", Respublika Tatarstan (RU)

( * ) Notice: Subject to any disclaimer, the term of this patent is extended or adjusted under 35 U.S.C. 154(b) by 0 days.

(21) Appl. No.: 17/101,590

(22) Filed: Nov. 23, 2020

(65) Prior Publication Data

US 2021/0077525 A1    Mar. 18, 2021

Related U.S. Application Data

(63) Continuation-in-part of application No. 16/904,986, filed on Jun. 18, 2020, now abandoned, which is a continuation of application No. 14/400,273, filed as application No. PCT/RU2013/000366 on Apr. 26, 2013, now abandoned.

(30) Foreign Application Priority Data

May 10, 2012   (RU) ............. RU2012119192

(51) Int. Cl.
| | |
|---|---|
| A61K 33/24 | (2019.01) |
| A61K 31/663 | (2006.01) |
| A61K 33/14 | (2006.01) |
| A61L 24/02 | (2006.01) |
| A61K 9/00 | (2006.01) |
| A61K 47/02 | (2006.01) |
| A61K 9/08 | (2006.01) |
| A61L 24/00 | (2006.01) |

(52) U.S. Cl.
CPC ............ *A61K 33/24* (2013.01); *A61K 9/0019* (2013.01); *A61K 9/08* (2013.01); *A61K 31/663* (2013.01); *A61K 33/14* (2013.01); *A61K 47/02* (2013.01); *A61L 24/0015* (2013.01); *A61L 24/02* (2013.01); *A61L 2430/02* (2013.01)

(58) Field of Classification Search
CPC ........ A61K 9/0019; A61K 9/08; A61K 33/24; A61K 31/663; A61K 33/06; A61K 33/14; A61K 47/02; A61K 2300/00; A61P 19/08; A61P 19/00; A61L 24/0015; A61L 24/02; A61L 2400/06; A61L 2430/02
See application file for complete search history.

(56) References Cited

U.S. PATENT DOCUMENTS

2015/0140119 A1 *  5/2015  Devyatov ............... A61P 19/00
                                                                424/617

FOREIGN PATENT DOCUMENTS

RU         2248210 C1 *  3/2005
WO    WO-2013169146 A1 * 11/2013  ............. A61K 47/02

OTHER PUBLICATIONS

English translation of RU-2248210-C1. Translation received from Google Patents, Apr. 21, 2022. (Year: 2022).*

* cited by examiner

*Primary Examiner* — Doan T Phan
(74) *Attorney, Agent, or Firm* — Nadya Reingand

(57) ABSTRACT

The invention relates to the treatment of different bone injuries, particularly fractures and fissure fractures. In order to reduce the time taken for bone tissue to regenerate at the site of damage, a method is used for regenerating bone tissue by fixing fragments of the damaged bone with a plaster cast or a bandage made of a polymer material and introducing into the fracture zone an aqueous solution containing 1-hydroxyethylidene diphosphonic acid in an amount of (1.80-2.06) g/l, anhydrous calcium chloride in an amount of (1.44-2.22) g/l, gadolinium (III) nitrate hexahydrate in an amount of (0.30-0.40) g/l and dysprosium (III) chloride hexahydrate in an amount of (0.038-0.076) g/l, with a pH of (7.3-7.8), wherein, prior to being introduced into the fracture zone, the above solution is brought to a temperature of (30-100°) C., is held at this temperature for (1-48) hours and is then cooled to room temperature.

1 Claim, 1 Drawing Sheet

METHOD FOR BONE TISSUE
REGENERATION IN EXPERIMENTS

CROSS-REFERENCE TO RELATED APPLICATIONS

The present application is a Continuation-in-Part of U.S. patent application Ser. No. 16/904,986, which, in turn, is a Continuation of U.S. patent application Ser. No. 14/400,273. The present application claims priority to and incorporates fully by reference all of the above-referenced patent applications.

FIELD OF THE INVENTION

The invention relates to the treatment of different bone injuries, particularly fractures and fissure fractures, and can be used in medical and veterinary therapy and surgery.

BACKGROUND OF THE INVENTION

A bone tissue regeneration method, wherein the injured bone fragments are immobilized with a plaster cast and Subsequent introduction of an aqueous solution comprising 1-hydroxyethylidene diphosphonic acid, calcium chloride, and gadolinium(III) nitrate into the bone fracture Zone at room temperature, is known in the art 1. The disadvantage of said method is relatively long bone tissue regeneration time.

A method comprising the cumulative features and the attained technical effect, which are most closely related to the object of the present invention, is the method for bone tissue regeneration in experiments comprising immobilization of the injured bone fragments with a plaster cast or plastic bandage and Subsequent introduction of an aqueous Solution with pH 7.3-7.8, comprising 1.80-2.06 g/L of 1-hydroxyeth ylidene diphosphonic acid, 1.44-2.22 g/L of anhydrous calcium chloride, 0.30-0.40 g/L of gadolinium (III) nitrate hexahydrate, and 0.038-0.076 g/L of dysprosium (III) chloride hexahydrate, into the bone fracture Zone at room temperature 2. The disadvantage of said method, taken as a prototype, is also relatively long bone tissue regeneration time.

The objective of the present invention is to further reduce the damaged or defected bone tissue regeneration time as well as time required to restore normal physiological function of the injured bone.

SUMMARY OF THE INVENTION

The stated objective is achieved as follows: in the existing method for bone tissue regeneration in experiments, wherein the injured bone fragments are immobilized with a plaster cast or plastic bandage, the aqueous Solution with pH 7.3-7.8 comprising 1.80-2.06 g/L of 1-hydroxyethylidene diphosphonic acid, 1.44-2.22 g/L of anhydrous calcium chloride, 0.30-0.40 g/L of gadolinium (III) nitrate hexahydrate, and 0.038-0.076 g/L of dysprosium (III) chloride hexahydrate is injected into the bone fracture Zone; however, prior to the injection thereof into the fracture Zone, said solution is brought to 30° C.-100° C., kept at said temperature for 1-48 hrs., and then brought back to room temperature. Employing said method of the present invention results in significant acceleration of bone tissue regeneration and further reduction (by 15-20%) of time required to restore normal physiological function of the injured bone in comparison to the method described in prototype 2.

DETAILED DESCRIPTION OF PREFERRED EMBODIMENTS

Figure 1:
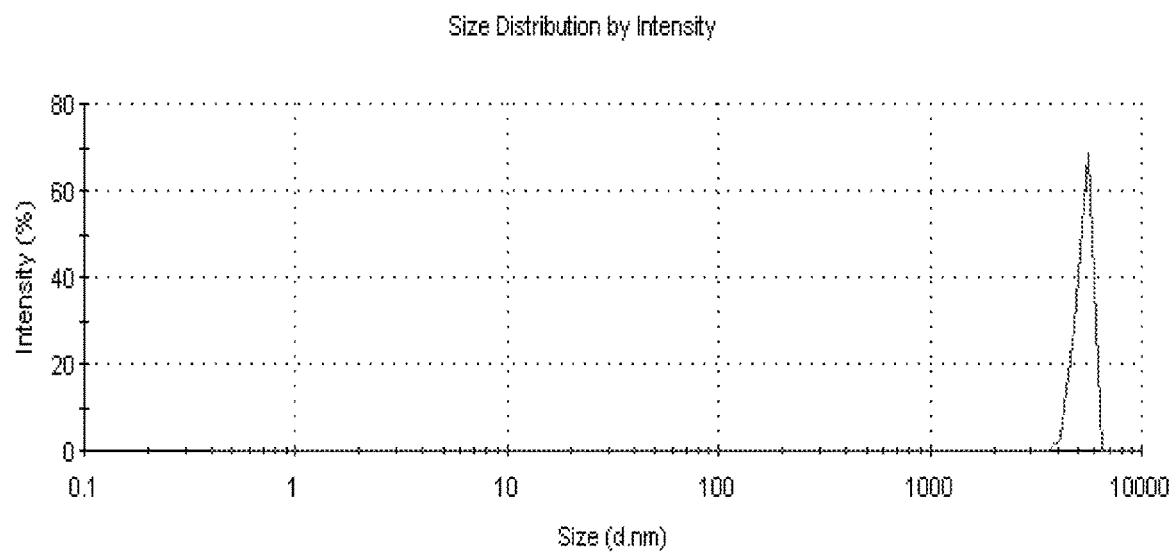
FIG. 1 shows data regarding the solid phase particle size distribution of the closest known prior art.

No method for bone tissue regeneration in experiments, wherein all features thereof would fully match the features of the present invention, has ever been disclosed in the literature. Thus, the present invention can be claimed to comply with the first criterion of the Russian Federation Patent Law, novelty. The significant time reduction in restoration of normal physiological function of the injured bone, which was observed in the experiment, relative to existing method 2, cannot be deduced from the comparison of the features of prototype 2 with the altered features, i.e., a prior heating of the solution used therein specifically to the aforementioned 30° C.-100° C. temperature and subsequent keeping said solution at said temperature specifically over the aforementioned (1-48 hrs.). Therefore, the claimed technical solution does not clearly follow from the prior art and thus, it complies with the second criterion of the Russian Federation Patent Law, inventive level. The claimed method of the present invention does not require any special equipment and can be easily realized even in an outpatient setting, thus, it also complies with the third criterion of the Russian Federation Patent Law, industrial applicability.

The claimed method for bone tissue regeneration in experiments can be further illustrated with the following examples:

EXAMPLE 1

Preparation of the Claimed Solution

A 1000 ml volumetric flask is filled with 1.80-2.06 g/L of 1-hydroxyethylidene diphosphonic acid, 1.44-2.22 g/L of anhydrous calcium chloride, 0.30-0.40 g/L of gadolinium (Ill) nitrate hexahydrate, 0.038-0.076 g/L of dysprosium (Ill) chloride hexahydrate, and 950 ml of distilled water. pH of the resulting mixture is brought to 7.3-7.8 with any concentrated alkaline Solution (such as 10% aqueous Sodium hydroxide solution). The resulting solution is brought to 1000 ml with distilled water, heated to 30° C.-100° C., kept at that temperature for 1-48 hrs., and then cooled down to room temperature (20-25° C.). The resulting solution is then used in the claimed method.

EXAMPLE 2

An aqueous solution with the following composition (g/L)

1-hydroxyethylidene diphosphonic acid 1.80
Anhydrous calcium chloride 1.44
Gadolinium (III) nitrate hexahydrate 0.30
Dysprosium (III) chloride hexahydrate 0.038, is prepared with pH 7.3, brought to 30° C., kept at said temperature for 48 hrs., then cooled to room temperature. Under anesthesia, 2 ml of the prepared solution are then injected over a period of 2 min. into the injured bones of a Northern European cat with lower hind leg fractures, which were induced one hour prior to the experiment. After injection, the fractured bone sites are immobilized in a plaster castor bandaged with plastic bandages, and the injured leg segments are kept as Such until recovery of locomotor function. Regeneration of the injured bone tissue is followed with X-rays, using a radiotransparent synthetic Lohmann&Rauscher Cellacast Xtra bandage or its analog, or cutting out special "windows' around the injury site. Bone tissue regeneration time is determined visually, based on the injured animals behavior (from the time of injection of the solution until the time of full locomotor function recovery of the injured bone with 12 hrs. accuracy). The indicator for this particular case study is shown in Table 1.

EXAMPLE 3

Follows the general procedure of Example 2, but for injection, using 2 ml of the aqueous solution with the following composition, g/L.
1-hydroxyethylidene diphosphonic acid 1.92
Anhydrous calcium chloride 1.88
Gadolinium (III) nitrate hexahydrate 0.35
Dysprosium (III) chloride hexahydrate 0.055,
with pH 7.5, which is then heated to 60° C., and kept at this temperature for 6 hrs. Bone tissue regeneration time for this case study is shown in Table 1.

EXAMPLE 4

Same as Example 2, but for injection, using 2 ml of the aqueous solution with the following composition, g/L:
1-hydroxyethylidene diphosphonic acid 1.92
Anhydrous calcium chloride 1.88
Gadolinium (III) nitrate hexahydrate 0.35
Dysprosium (III) chloride hexahydrate 0.055,
with pH 7.7, which is then heated to 70° C., and kept at this temperature for 4 hrs. Bone tissue regeneration time for this case study is shown in Table 1.

EXAMPLE 5

Follows the general procedure of Example 2, but for injection, using 2 ml of the aqueous solution with the following composition, g/L.
1-hydroxyethylidene diphosphonic acid 2.06
Anhydrous calcium chloride 2.20
Gadolinium (III) nitrate hexahydrate 0.40
Dysprosium (III) chloride hexahydrate 0.076,
with pH 7.8, which is then heated to 100° C., and kept at this temperature for 1 hr. Bone tissue regeneration time for this case study is shown in Table 1.

EXAMPLE 6

Same as Example 2, but for injection, using 2 ml of the aqueous solution with the following composition, g/L:
1-hydroxyethylidene diphosphonic acid 1.80
Anhydrous calcium chloride 1.44
Gadolinium (III) nitrate hexahydrate 0.30
Dysprosium (III) chloride hexahydrate 0.038,
with pH 7.5, which is then heated to 70° C., and kept at this temperature for 4 hrs. Bone tissue regeneration time for this case study is shown in Table 1.

EXAMPLE 7

Same as Example 2, but for injection, using 2 ml of the aqueous solution with the following composition, g/L:
1-hydroxyethylidene diphosphonic acid 1.80
Anhydrous calcium chloride 1.44
Gadolinium (III) nitrate hexahydrate 0.30
Dysprosium (III) chloride hexahydrate 0.038,
with pH 7.8, which is then heated to 70° C., and kept at this temperature for 4 hrs. Bone tissue regeneration time for this case study is shown in Table 1.

EXAMPLE 8

Comparative. Same as Example 3, but with pH of the solution at 7.0, Bone tissue regeneration time for this case study is shown in Table 1.

EXAMPLE 9

Comparative. Same as Example 3, but with pH of the solution at 8.0. Bone tissue regeneration time for this case study is shown in Table 1.

EXAMPLE 10

Comparative. Same as Example 5, but the solution is kept at the temperature mentioned therein for 0.5 hrs. Bone tissue regeneration time for this case study is shown in Table 1.

EXAMPLE 11

Comparative. Same as Example 2, but the solution is kept at the temperature mentioned therein for 60 hrs. Bone tissue regeneration time for this case study is shown in Table 1.

EXAMPLE 12

Analogous to Background Example [1]. Follows the general procedure of Example 2, but for injection, using 2 ml of the aqueous solution with the following composition, g/L.
1-hydroxyethylidene diphosphonic acid 2.00
Anhydrous calcium chloride 2.20
Gadolinium (III) nitrate hexahydrate 0.40,
with pH 8.0, and omitting the steps of heating the solution to 30° C. and keeping it at said temperature. Bone tissue regeneration time for this case study is shown in Table 1.

EXAMPLE 13

Based on Background Example [2]. Same as Example 3, using the same composition of the solution and same pH, but omitting the steps of bringing the solution to 60° C. and keeping it at said temperature. Bone tissue regeneration time for this case study is shown in Table 1.

EXAMPLE 14

Based on Background Example [2]. Same as Example 4, using the same composition of the Solution and same pH, but omitting the steps of heating the solution to 70° C., and keeping it at said temperature. Bone tissue regeneration time for this case study is shown in Table 1.

EXAMPLE 15

Based on Background Example [2]. Same as Example 5, using the same composition of the Solution and same pH, but omitting the steps of heating the solution to 100° C. and keeping it at said temperature. Bone tissue regeneration time for this case study is shown in Table 1.

TABLE 1

| Example # | Injured Animal | Time to restore full locomotor function of the injured bone segment, days |
|---|---|---|
| 2 | Northern European Cat | 5.0 |
| 3 | Northern European Cat | 4.5 |
| 4 | Northern European Cat | 4.5 |
| 5 | Northern European Cat | 5.0 |
| 6 | Northern European Cat | 4.5 |
| 7 | Northern European Cat | 5.0 |
| 8 (comparative) | Northern European Cat | 6.0 |
| 9 (comparative) | Northern European Cat | 6.5 |
| 10 (comparative) | Northern European Cat | 6.0 |
| 11 (comparative) | Northern European Cat | 4.5 |
| 12 (analog) | Northern European Cat | 9.0 |
| 13 (prototype) | Northern European Cat | 6.0 |
| 14 (prototype) | Northern European Cat | 6.5 |
| 15 (prototype) | Northern European Cat | 6.0 |

EXAMPLE 16

An Aqueous Solution with the Following Composition (g/L)

1-hydroxyethylidene diphosphonic acid 1.80

Anhydrous calcium chloride 1.44

Gadolinium (III) nitrate hexahydrate 0.30

Dysprosium (III) chloride hexahydrate 0.038, is prepared with pH 7.3, then brought to 30° C., and kept at said temperature for 48 hrs., after which it is cooled to room temperature. Under anesthesia, the prepared solution is then administered to a rabbit of unspecified breed, whose both femurs have been injured by drilling with an electric drill, 5 mm in diameter, under general anesthesia. However, in this experiment, 1 ml of said solution (over a period of 2 min., as in Example 2) is injected into the injury site of only one of the injured femurs (the second analogous bone is used as control). After that, all injury sites are immobilized in a plastercast or bandaged with plastic bandages, and followed with X-rays for bone tissue regeneration, same as in Example 2. Bone tissue regeneration time is determined visually, based on the injured animal's behavior (from the time of injection of the solution until the time of full recovery of locomotor function of the injured bone with 12 hrs. accuracy). The indicator for this particular case study is shown in Table 2.

EXAMPLE 17

Follows the general procedure of Example 16, but for injection, using the aqueous Solution prepared in the same composition and by the same procedure as described in Example 3.

EXAMPLE 18

Follows the general procedure of Example 16, but using the aqueous solution for injection that has been prepared in the same composition and by the same procedure as described in Example 4.

EXAMPLE 19

Follows the general procedure of Example 16, but for injection, using the aqueous Solution prepared in the same composition and by the same procedure as described in Example 5.

EXAMPLE 20

Follows the general procedure of Example 16, but for injection, using the aqueous Solution prepared in the same composition and by the same procedure as described in Example 6.

EXAMPLE 21

Follows the general procedure of Example 16, but for injection, using the aqueous Solution prepared in the same composition and by the same procedure as described in Example 7.

EXAMPLE 22. COMPARATIVE

Follows the general procedure of Example 16, but for injection, using the aqueous Solution prepared in the same composition and by the same procedure as described in Example 8.

EXAMPLE 23. COMPARATIVE

Follows the general procedure of Example 16, but for injection, using the aqueous Solution prepared in the same composition and by the same procedure as described in Example 9.

EXAMPLE 24. COMPARATIVE

Follows the general procedure of Example 16, but for injection, using the aqueous Solution prepared in the same composition and by the same procedure as described in Example 10.

EXAMPLE 25. COMPARATIVE

Follows the general procedure of Example 16, but for injection, using the aqueous Solution prepared in the same composition and by the same procedure as described in Example 11.

EXAMPLE 26

Analogous to Background Example [1]. Follows the general procedure of Example 16, but for injection, using the aqueous Solution prepared in the same composition and by the same procedure as described in Example 12.

EXAMPLE 27

Based on Background Example [2]. Follows the general procedure of Example 16, but for injection, using the aqueous Solution prepared in the same composition and by the same procedure as described in Example 13.

EXAMPLE 28

Based on Background Example [2]. Follows the general procedure of Example 16, but for injection, using the aqueous Solution prepared in the same composition and by the same procedure as described in Example 14.

EXAMPLE 29

Based on Background Example [2]. Follows the general procedure of Example 16, but for injection, using the aqueous Solution prepared in the same composition and by the same procedure as described in Example 15.

Data comparing regeneration times of bone tissue, which have been previously injected with solutions as described in Examples 16-29, and regeneration times of bone tissue that haven't been injected with said solutions are shown in Table 2.

TABLE 2

| | | Time to restore full locomotor function of the injured bone segment, days | |
| --- | --- | --- | --- |
| Example # | Injured Animal | For the bone injected with the solution | For control |
| 16 | Unspecified Breed Rabbit | 4.0 | 18.0 |
| 17 | Unspecified Breed Rabbit | 3.5 | 17.5 |
| 18 | Unspecified Breed Rabbit | 4.0 | 18.0 |
| 19 | Unspecified Breed Rabbit | 4.0 | 18.0 |
| 20 | Unspecified Breed Rabbit | 4.0 | 17.5 |
| 21 | Unspecified Breed Rabbit | 3.5 | 18.0 |
| 22 (comparative) | Unspecified Breed Rabbit | 4.5 | 18.0 |
| 23 (comparative) | Unspecified Breed Rabbit | 4.5 | 17.5 |
| 24 (comparative) | Unspecified Breed Rabbit | 4.5 | 17.5 |
| 25 (comparative) | Unspecified Breed Rabbit | 4.0 | 18.0 |
| 26 (analog) | Unspecified Breed Rabbit | 8.5 | 18.0 |
| 27 (prototype) | Unspecified Breed Rabbit | 5.0 | 17.5 |
| 28 (prototype) | Unspecified Breed Rabbit | 5.0 | 18.0 |
| 29 (prototype) | Unspecified Breed Rabbit | 5.5 | 18.5 |

EXAMPLE 30

An aqueous solution with the same composition as that of Example 3 is prepared following the same procedure. Under anesthesia, 2.5 ml of said solution are administered over a 2 min. period to a stray mutt 6 hrs. after inducing a significantly displaced right front humeral fracture. After that, the injury site is immobilized in a plaster cast or bandaged with plastic bandages. Bone tissue regeneration is followed as described in Example 2. Bone tissue regeneration time is determined visually, based on the injured animals behavior (from the time of injection of the solution until the time of full recovery of locomotor function of the injured bone with 12 hrs. accuracy). The indicator for this particular case study is shown in Table 3.

EXAMPLE 31

Follows the general procedure of Example 30, but for injection, using the aqueous Solution prepared in the same composition and by the same procedure as described in Example 4.

EXAMPLE 32. COMPARATIVE

Follows the general procedure of Example 30, but for injection, using the aqueous Solution prepared in the same composition and by the same procedure as described in Example 10.

EXAMPLE 33. COMPARATIVE

Follows the general procedure of Example 30, but for injection, using the aqueous Solution prepared in the same composition and by the same procedure as described in Example 11.

EXAMPLE 34

Based on Background Example [2]. Follows the general procedure of Example 30, but for injection, using the aqueous Solution prepared in the same composition and by the same procedure as described in Example 14.

EXAMPLE 35

Based on Background Example [2]. Follows the general procedure of Example 30, but for injection, using the aqueous Solution prepared in the same composition and by the same procedure as described in Example 15.

Bone tissue regeneration time data when using technologies described in Examples 30-35 are shown in Table 3.

TABLE 3

| Example # | Injured Animal | Time to restore full locomotor function of the injured bone segment, days |
| --- | --- | --- |
| 30 | Stray mutt | 7.5 |
| 31 | Stray mutt | 8.0 |
| 32 (comparative) | Stray mutt | 9.0 |
| 33 (comparative) | Stray mutt | 8.0 |
| 34 (prototype) | Stray mutt | 10.5 |

The data in Tables 1-3 clearly demonstrate that the method of the present invention significantly reduces the time of bone tissue regeneration at the injury site (20-25%) as compared to prototype method 2, and said reduction was observed in all injured animals irrespective of the type. Equally important are the temperature range (30-100° C.) and the thermostating time (1-48 hrs.) at any of the temperatures of said range, as well as the solution's pH (7.3-7.8); and going outside of either lower or upper limit of said range usually results in increased bone tissue regeneration time (keeping the solution at the specified temperature longer shows no real changes in the earlier achieved indicators; therefore, increasing the time beyond 48 hrs. does not really lead to any significant changes). Our measurements of the regenerated bone tissue's strength showed no noticeable differences observed when using methods known in the art [1, 2] or the regeneration method of the present invention. The blood count data of the animals during regeneration of the injured bone tissue and observation of the injured animals' subjective states during the treatment thereof (appetite, response, etc.) did not show any expressive toxicity of the claimed solution for injection; and also, none of the ingredients comprising said solution for injection is toxic, as per [3, 4]. In conclusion, the claimed solution has a long shelf life and can be kept for a long time (at least 1 year) in a sealed container with no loss in the performance thereof.

The solution provided via the method of the present invention is an aqueous heterogeneous solution. The solution provided is also a non-polymer solution (i.e. it does not comprise any polymers). Furthermore, the water solution is a non-colloidal suspension. Even further, the solution comprises a medicament. Therefore, the solution provided is an "aqueous non-polymer non-colloidal solution" further comprising a medicament. The prior art solely discusses colloidal systems/solutions and does not teach the inclusion of a drug within a non-colloidal suspension such as the solution provided via the present invention (see, e.g., US Patent Pub. No. 2006/0014938 A1, Para. 58). That publication, for example, specifically speaks of colloid suspensions which can withstand heating, and does not discuss any other types of suspensions, e.g., the present application's suspension, which is a non-colloidal suspension.

The heating step of the method discussed above and throughout this description is a significant and nonobvious step which increases the effectiveness of the medicament substantially and recognizably. The results obtained, as shown in the Tables herein, as well as in FIGS. 1 & 2, were greater than expected. The prior art does not teach or suggest heating in order to increase the effectiveness of any drug—instead, the prior art within this field is concerned with heating a molecular solution to either form the colloidal solution or sterilize the colloidal solution. Furthermore, any prior art colloidal solutions from the distinct field of medical imaging are also inapplicable to the instant field of invention, which relates to methods for bone tissue regeneration. In addition, it was experimentally determined that the heating step leads to a significantly greater efficacy in the bone treatment and regeneration time needed due to a smaller particle size after heating. In comparison, the standard procedure for sterilization using saturated steam, at a temperature of 120-122° C., under a pressure of 120 kPa, for 8 minutes, fails to achieve the same efficacy.

Regarding said significantly greater efficacy, it was the heating step of the present invention which, as later determined, caused the particles within the solution to exhibit an unexpected result. The suspended particles became smaller as a result of the heating, instead of the expected result of the particles becoming larger. The expected results from heating a suspension would be particle enlargement, particle aggregation, and a decrease in sedimentation stability. These expected results can be explained, e.g., by the fact that increasing a temperature leads to an increase in the intensity of Brownian motion. Thus, under heating, the suspended particles would be expected to collide with each other more often and at faster velocities. The increase of particle velocities and collisions would, in turn, be expected to lead to an increase in the size of solid-phase particles being formed. As a result, the larger particles would settle faster to the bottom of a vessel (i.e., the sedimentation time decreases and/or the sedimentation rate increases).

Figure 2:
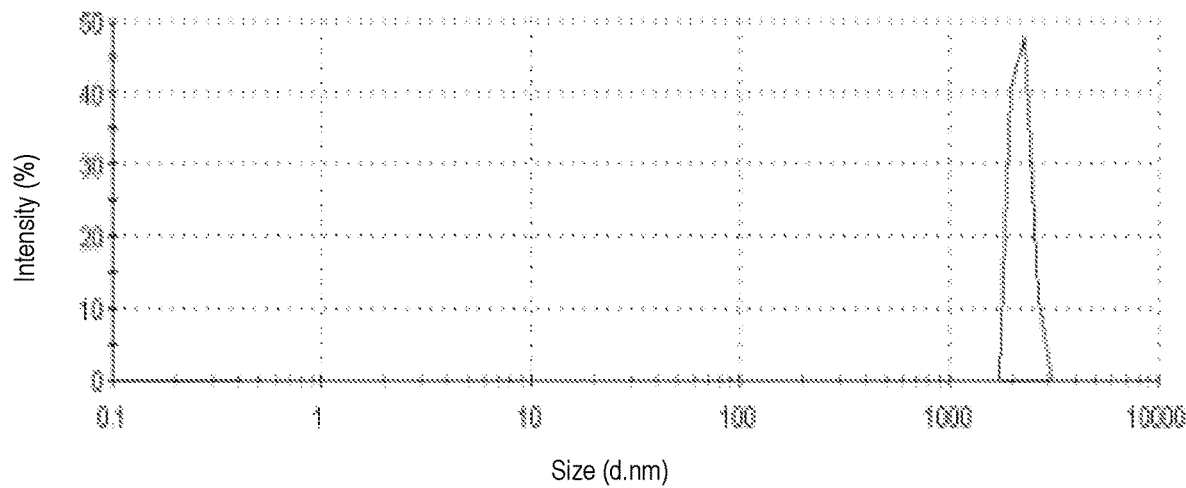
FIG. 2 shows data regarding the solid phase particle size distribution within the solution resulting from the present invention.

In contrast to what was expected, after heating the suspension of the present invention, a decrease in the sedimentation rate was observed (i.e. less sediment was observed over the same time unit), which indicated a decrease in particle size. This unexpected result of decreased particle sizes after heating led to the inventors' realization that the smaller particles formed by the heating step most likely experienced an increased rate of entering target cell membranes of a patient. See, e.g., the comparison between FIGS. 1 & 2, where FIG. 1 shows the average particle size without heating, and where FIG. 2 shows the average particle size with heating. This result led to two conclusions: (1) that the particles within the solution were smaller, since, e.g., slower sedimentation occurred due to the heating; and (2) the lower sedimentation further increased the consumption rate of active components, thus forming a more effective drug solution which is thereafter administered to a patient. In summary, smaller, not larger, particles are formed as a result of the heating. Since the mass of the solid phase remains unchanged, the result must be that there are more solid-phase particles, each of the particles having a smaller size than anticipated. The resulting solution thereby comprises the solid-phase material (i.e. particles) being equally available but even more finely dispersed within the smaller sized particles.

The smaller particles resulting from heating directly oppose the expected result of heating, which would be greater precipitation and larger sized suspended particles, if any change in particle size is expected. Such expectations may be drawn from any of the examples provided above. In direct contrast, FIGS. 1 and 2 provide examples of experimental data obtained, determining the size of crystallites in a suspension as well as the polydispersity indices (PdIs) in a suspension (by the method of dynamic light scattering (DLS) on «Malvern» Zetasizer Nano ZS device) not subjected to thermal treatment (i.e. heating) (FIG. 1) the suspension after being subjected to thermal treatment (i.e. heating) (FIG. 2). In FIG. 1, the average particle size of the solid phase is 5,320 nm (i.e., 5.3 microns), and the polydispersity index (PdI) is 0.091 (i.e., the solid phase is practically mono-disperse). In FIG. 2, the average particle size of the solid phase is 2,220 nm (i.e., 2.2 microns), and the polydispersity index (PdI) is 0.368 (i.e., the solid phase is highly polydisperse). In comparison, FIGS. 1-2 show particular particle size measurements combined in a distribution. The analysis of more than 20 particle size measurements, for each of the figures, clearly indicates that the size of the solid particles after thermal treatment (i.e. heating), in the "temperature-time" bond, decreases by about one half, while the same particles' polydispersity significantly increases also as a result of the same heating. Such an opposite effect of thermal action on the solution/suspension remains unexplained and remains the subject of further testing.

Since heating previously implied larger sized particles, which would lead to a lower rate of active components entering target cells, a heating step prior to treatment was previously considered ineffective. In direct contrast, however, the particles of the present invention had an increased rate of effective delivery to target cells, particularly due to their unexpectedly smaller size, a size which was a direct result of the heating step.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary"

is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for bone tissue regeneration, comprising:
preparing an aqueous solution comprising 1.80-2.06 g/L of 1-hydroxyethylidene diphosphonic acid, 1.44-2.22 g/L of anhydrous calcium chloride, 0.30-0.40 g/L of gadolinium (III) nitrate hexahydrate, and 0.038-0.076 g/L of dysprosium (III) chloride hexahydrate, said aqueous solution having a pH of 7.3-7.8,
heating the solution to a temperature between 30° C. and 100° C., keeping said solution at said temperature for 1-48 hours, then cooling the solution to room temperature,
immobilizing injured bone fragments in a first plaster cast, and
injecting the solution into a bone fracture area and reducing a time of bone tissue regeneration to 3.5-4 days.

* * * * *